(12) United States Patent
Yang et al.

(10) Patent No.: US 7,552,501 B2
(45) Date of Patent: Jun. 30, 2009

(54) FINGER WIPE WITH IMPROVED SEAM STRUCTURE

(75) Inventors: Kaiyuan Yang, Cumming, GA (US);
Jeffrey E. Fish, Dacula, GA (US);
Shawn R. Feaster, Duluth, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 759 days.

(21) Appl. No.: 11/118,078

(22) Filed: Apr. 29, 2005

(65) Prior Publication Data
US 2006/0242780 A1 Nov. 2, 2006

(51) Int. Cl.
*A41D 13/08* (2006.01)
*A47L 13/18* (2006.01)

(52) U.S. Cl. .................. 15/227; 2/21; 2/163
(58) Field of Classification Search .......... 2/21, 2/163; 15/227
See application file for complete search history.

(56) References Cited

U.S. PATENT DOCUMENTS

| | | |
|---|---|---|
| 3,338,992 A | 8/1967 | Kinney |
| 3,341,394 A | 9/1967 | Kinney |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 4,100,324 A | 7/1978 | Anderson et al. |
| 4,340,563 A | 7/1982 | Appel et al. |
| 4,374,888 A | 2/1983 | Bornslaeger |
| 4,443,513 A | 4/1984 | Meitner et al. |
| 4,652,487 A | 3/1987 | Morman |
| 4,655,760 A | 4/1987 | Morman et al. |
| 4,657,802 A | 4/1987 | Morman |
| 4,660,228 A | 4/1987 | Ogawa et al. |
| 4,720,415 A | 1/1988 | Vander Wielen et al. |
| 4,781,966 A | 11/1988 | Taylor |
| 4,789,699 A | 12/1988 | Kieffer et al. |
| 4,818,464 A | 4/1989 | Lau |
| 4,965,122 A | 10/1990 | Morman |
| 4,981,747 A | 1/1991 | Morman |
| 5,036,551 A | 8/1991 | Dailey et al. |
| 5,068,941 A | 12/1991 | Dunn |
| 5,112,900 A | 5/1992 | Buddenhagen et al. |
| 5,114,781 A | 5/1992 | Morman |
| 5,226,992 A | 7/1993 | Morman |
| 5,244,482 A | 9/1993 | Hassenboehler, Jr. et al. |
| 5,336,545 A | 8/1994 | Morman |
| 5,348,153 A | 9/1994 | Cole |

(Continued)

FOREIGN PATENT DOCUMENTS

WO 9531154 11/1995

*Primary Examiner*—Mark Spisich
(74) *Attorney, Agent, or Firm*—Dority & Manning, P.A.

(57) ABSTRACT

A finger cover, such as a finger wipe that can fit onto a human finger, is provided with an improved seam structure. The cover includes a pocket member having an open end for the insertion of a finger. The pocket member is formed by a first panel attached to a second panel along a flush outwardly facing circumferential edge seam. The seam is less than about 1 millimeter (mm) in width and about 1 mm in height. Additional reinforcing weld points may be provided at various locations along the seam.

9 Claims, 7 Drawing Sheets

U.S. PATENT DOCUMENTS

| | | | |
|---|---|---|---|
| 5,385,775 | A | 1/1995 | Wright |
| 5,407,715 | A | 4/1995 | Buddenhagen et al. |
| 5,445,825 | A | 8/1995 | Copelan et al. |
| 5,524,764 | A | 6/1996 | Kaufman et al. |
| 5,587,225 | A | 12/1996 | Griesbach et al. |
| 5,649,336 | A * | 7/1997 | Finch et al. ............... 15/104.94 |
| 5,761,743 | A * | 6/1998 | Andrews et al. .................. 2/21 |
| 5,900,452 | A | 5/1999 | Plamthottam |
| 6,288,159 | B1 | 9/2001 | Plamthottam |
| 6,647,549 | B2 | 11/2003 | McDevitt et al. |
| 6,721,987 | B2 | 4/2004 | McDevitt et al. |
| 6,772,441 | B2 | 8/2004 | Lucas, Jr. |
| 6,898,819 | B2 * | 5/2005 | Tanaka et al. .................. 15/227 |
| 2002/0104608 | A1 | 8/2002 | Welch et al. |
| 2004/0005832 | A1 | 1/2004 | Neculescu et al. |
| 2004/0005835 | A1 | 1/2004 | Zhou et al. |
| 2004/0054341 | A1 | 3/2004 | Kellenberger et al. |
| 2004/0214494 | A1 | 10/2004 | Murphy et al. |
| 2004/0244132 | A1 * | 12/2004 | Ouellette et al. .............. 15/227 |
| 2005/0127578 | A1 | 6/2005 | Triebes et al. |
| 2005/0130522 | A1 | 6/2005 | Yang et al. |
| 2006/0009104 | A1 | 1/2006 | Schneider et al. |
| 2006/0143767 | A1 | 7/2006 | Yang et al. |
| 2006/0228969 | A1 | 10/2006 | Erdman |
| 2006/0242780 | A1 | 11/2006 | Yang et al. |
| 2007/0083980 | A1 | 4/2007 | Yang et al. |

\* cited by examiner

FINGER WIPE WITH IMPROVED SEAM STRUCTURE

BACKGROUND OF THE INVENTION

Finger wipes or covers are known and used in the art for a variety of purposes. A common use of finger wipes (also know as a "finger glove" in the art) is for applying ointments, medications, alcohol, oral anesthetics, and the like, to various body parts. Such devices may also be utilized to remove various substances, such as makeup, or to clean body parts or other objects.

Finger wipes have proven particularly useful in the field of dental hygiene in that they provide a portable and efficient means for more frequent dental care, and as a cleaning device that can be easily used in public. In particular, a number of finger-mounted teeth cleaning devices have been developed that can be placed over a finger and wiped over the teeth and gums. These devices are typically small, portable, and disposable.

Examples of oral cleaning devices and finger wipes are disclosed, for instance, in U.S. Pat. No. 6,721,987 to McDevitt, et al. and in U.S. Pat. No. 6,647,549 also to McDevitt, et al., which are incorporated herein by reference. An oral hygiene finger device is also described in U.S. Pat. No. 5,445,825 to Copelan et al. Other finger-mounted teeth cleaning devices were developed to contain an elastomeric material to help prevent the device from slipping or falling off the user's finger during cleaning. Examples of such teeth cleaning devices are disclosed in U.S. Pat. No. 5,068,941 to Dunn; U.S. Pat. No. 5,348,153 to Cole; U.S. Pat. No. 5,524,764 to Kaufman et al.; and PCT Publication No. WO 95/31154 to Mittiga et al.

For various economic and manufacturing reasons, it may be desired to produce the finger wipes from separate opposed layers or panels of material that are subsequently bonded together by suitable techniques. However, the cut edge or seam line of a non-woven laminate, especially near bonds, can have a considerable stiffness. With finger wipes, which are often used against sensitive body parts, the stiffness is undesirable in that it increases the potential for abrasions, cuts, and irritation from use of the finger wipe. In order to make the seam line of conventional wipes soft and more tolerable, the bonded area may be further treated, such as by creating microcuts along the seam. Alternately, the product may undergo an "inside-out" inversion so that the seam line is located inside of the finger wipe, as described in U.S. Pat. No. 6,647,549 B2.

Obviously, adding a cutting procedure or an inside-out conversion process inevitably increases the production cost and may make the product(s) economically uncompetitive to manufacture. Additionally, microcuts along the seam may not be desirable because sharp cuts along the seam may still injure or irritate sensitive body parts, such as the user's gum. Furthermore, microcuts along the seam may create undesirable residues or particles along the seam that can be transferred into the user's mouth or other body parts. Additionally, conventional cutting methods may be inadequate for producing clean cuts. For example, mechanical cutting can produce solid residues. A water-knife may contaminate the nonwoven surface, wash-out potential therapeutic agents, and also require a drying step. Laser cutting can produce stiff seams, and potentially hard cutting edges, from local burning.

Accordingly, there is a need to develop a finger wipe with an improved seam structure.

DEFINITIONS

As used herein, the term "breathable" means pervious to water vapor and gases. In other words, "breathable barriers" and "breathable films" allow water vapor to pass therethrough, but are substantially impervious to liquid water. For example, "breathable" can refer to a film or laminate having water vapor transmission rate (WVTR) of at least about 300 $g/m^2/24$ hours measured using ASTM Standard E96-80, upright cup method, with minor variations as described in the following Test Procedure.

A measure of the breathability of a fabric is the water vapor transmission rate (WVTR) which, for sample materials, is calculated essentially in accordance with ASTM Standard E96-80 with minor variations in test procedure as set forth in detail in the '549 patent incorporated herein by reference.

As used herein, the terms "elastic" and "elastomeric" are generally used to refer to materials that, upon application of a force, are stretchable to a stretched, biased length which is at least about 125%, or one and a third times, its relaxed, unstretched length, and which will retract at least about 50% of its elongation upon release of the stretching, biasing force.

As used herein, "meltblown fibers" refers to fibers formed by extruding a molten thermoplastic material through a plurality of fine, usually circular, die capillaries as molten threads or filaments into converging high velocity, usually hot, gas (e.g. air) streams which attenuate the filaments of thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, et al. Meltblown fibers are microfibers which may be continuous or discontinuous, are generally smaller than 10 microns in average diameter, and are generally tacky when deposited on a collecting surface.

As used herein, a "liquid impermeable layer" refers to any material that is relatively impermeable to the transmission of fluids, i.e. a fabric having a liquid impermeable layer can have a blood strikethrough ratio of 1.0 or less according to ASTM test method 22.

As used herein, the term "neck-bonded" refers to an elastic member being bonded to a non-elastic member while the non-elastic member is extended in the machine direction creating a necked material. "Neck-bonded laminate" refers to a composite material having at least two layers in which one layer is a necked, non-elastic layer and the other layer is an elastic layer thereby creating a material that is elastic in the cross direction. Examples of neck-bonded laminates are such as those described in U.S. Pat. Nos. 5,226,992; 4,981,747; 4,965,122; and 5,336,545, all to Morman, all of which are incorporated herein by reference thereto.

As used herein, "spunbond fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel, et al.; U.S. Pat. No. 3,692,618 to Dorschner, et al.: U.S. Pat. No. 3,802,817 to Matsuki, et al.; U.S. Pat. No. 3,338,992 to Kinney; U.S. Pat. No. 3,341,394 to Kinney; U.S. Pat. No. 3,502,763 to Hartman; and U.S. Pat. No. 3,542,615 to Dobo, et al. Spunbond fibers are generally not tacky when they are deposited on a collecting surface. Spunbond fibers are generally continuous and have average diameters (from a sample of at least 10) larger than 7 microns, and more particularly, between about 10 and 40 microns.

As used herein, the term "stretch-bonded" refers to a composite material having at least two layers in which one layer is a gatherable layer and the other layer is an elastic layer. The layers are joined together when the elastic layer is in an extended condition so that upon relaxing the layers, the gatherable layer is gathered. For example, one elastic member can be bonded to another member while the elastic member is extended at least about 25 percent of its relaxed length. Such a multilayer composite elastic material may be stretched until the nonelastic layer is fully extended. One type of stretch-bonded laminate is disclosed, for example, in U.S. Pat. No. 4,720,415 to Vander Wielen, et al., which is incorporated herein by reference. Other composite elastic materials are described and disclosed in U.S. Pat. No. 4,789,699 to Kieffer, et al.; U.S. Pat. No. 4,781,966 to Taylor; U.S. Pat. No. 4,657,802 to Morman; and U.S. Pat. No. 4,655,760 to Morman, et al., all of which are incorporated herein by reference thereto.

As used herein, the term "texturized" refers to a base web having projections from a surface of the web in the Z-direction. The projections can have a length, for instance, from about 0.1 mm to about 25 mm, particularly from about 0.1 mm to about 5 mm, and more particularly from about 0.1 mm to about 3 mm. The projections can take on many forms and can be, for instance, bristles, tufts, loop structures such as the loops used in hook and loop attachment structures, and the like.

As used herein, the term "coform web" refers to a material produced by combining separate polymer and additive streams into a single deposition stream in forming a nonwoven web. Such a process is taught, for example, by U.S. Pat. No. 4,100,324 to Anderson, et al. which is hereby incorporated by reference.

SUMMARY

Objects and advantages of the invention will be set forth below in the following description, or may be obvious from the description, or may be learned through practice of the invention.

The present disclosure is generally directed to a finger cover, including, but not limited to, dental hygiene finger wipes. For ease of description only, aspects of the invention are explained herein by reference to finger wipe embodiments of the invention. However, it should be appreciated that the invention is not limited to finger wipes, and includes all embodiments of finger covers incorporating the novel aspects of the invention.

The finger cover generally is a disposable, absorbent or non-absorbent article that fits on one or more finger. In a particular embodiment, the cover is a finger wipe configured as a dental wipe that can fit onto a human finger for cleaning the teeth or gums of a person or animal. For instance, the dental wipe can be used by an individual to clean one's teeth or to clean the teeth of someone else, such as an infant, an elderly person, or a pet. Further, the dental wipe is particularly well suited for use by small children learning how to clean their teeth.

Besides being used to clean the teeth or gums of the user, a finger wipe of the present invention can also be used in other applications. For instance, the finger wipe may be used to clean or treat other parts of the body such as the eyes, the ears, the nose, and the like. The finger wipe may be used to apply a medicine, lotion, ointment, or the like to any part of the body. The finger wipe may also be used to apply or remove cosmetics to the face.

In still other embodiments, the finger wipe can be used to clean various utensils, objects or surfaces and/or to polish various items. For example, in one embodiment, the finger wipe can be used to polish silver.

The finger wipes can be made from numerous different types of materials. For instance, in one embodiment, non-woven webs made from synthetic and/or pulp fibers may be used. When used as an oral cleaning device, the finger wipe may include a texturized surface adapted to scrub or brush the teeth or gums of a user. Further, the finger wipe can also include an elastic component for providing the wipe with form-fitting properties. A moisture barrier, such as a liquid impermeable layer, may be incorporated into the finger wipe to prevent any fluids from contacting the wearer's fingers. In general, a moisture barrier refers to any barrier, layer, or film that is relatively liquid impervious. The moisture barrier prevents the flow of liquid through the finger wipe so that a user's finger remains dry when the wipe is being used. In some embodiments, the moisture barrier can remain breathable, i.e., permeable to vapors, such that a finger within the wipe is more comfortable. Examples of suitable moisture barriers can include films, fibrous materials, laminates, and the like. The wipe may include an elastic nonwoven material having form-fitting properties to help the wipe effectively fit onto a finger. Suitable materials will be described in greater detail below.

A finger wipe of the present invention can generally be formed in a variety of ways. For instance, the finger wipe can be formed from two or more sections or panels of the same or a different material, depending on the desired characteristics of the finger wipe. For example, in one embodiment, the finger wipe is formed from two panel sections, wherein one section may be formed from a textured nonwoven material and the other section may be formed from an elastomeric nonwoven material. A seam is formed around the closed periphery portion of the wipe to define an elongated closed-end tubular structure having a finger insertion opening at one end. The seams are produced so as to be strong while remaining pliable so as to present a "soft" feel to the user, and do not require additional processing or inversion of the finger wipe. The seams are described in greater detail in the following description.

Various additives can also be applied, if desired, to the finger wipe during manufacturing and/or by the consumer. For example, cationic materials, such as chitosan (poly-N-acetylglucosamine), chitosan salts, cationic starches, etc., can be applied to a wipe of the present invention to help attract negatively charged bacteria and deleterious acidic byproducts that accumulate in plaque. Examples of other suitable additives include, but are not limited to, dental agents, such as fluorides, peppermint oil, mint oil and alcohol mixtures; flavoring agents, such as xylitol; anti-microbial agents; polishing agents; hemostatic agents; surfactants; anti-ulcer components; and the like.

Additives can be applied to the finger wipes in the form of an aqueous solution, non-aqueous solution (e.g., oil), lotions, creams, suspensions, gels, etc. When utilized, the aqueous solution may be coated, saturated, sprayed, or impregnated into the wipe. In some embodiments, the additives can be applied asymmetrically. Moreover, in some instances, it may be desired that the additives comprise less than about 100% by weight of the wipe, and in some embodiments, less than about 50% by weight of the wipe, and particularly less than 10% by weight of the wipe.

It should be noted that any given range presented herein is intended to include any and all lesser included ranges. For example, a range of from 45-90 would also include 50-90; 45-80; 46-89 and the like. Thus, the range of 95% to 99.999% also includes, for example, the ranges of 96% to 99.1%, 96.3% to 99.7%, and 99.91 to 99.999%.

Various features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth in the specification, which makes reference to the appended drawings, in which.

Figure 1:
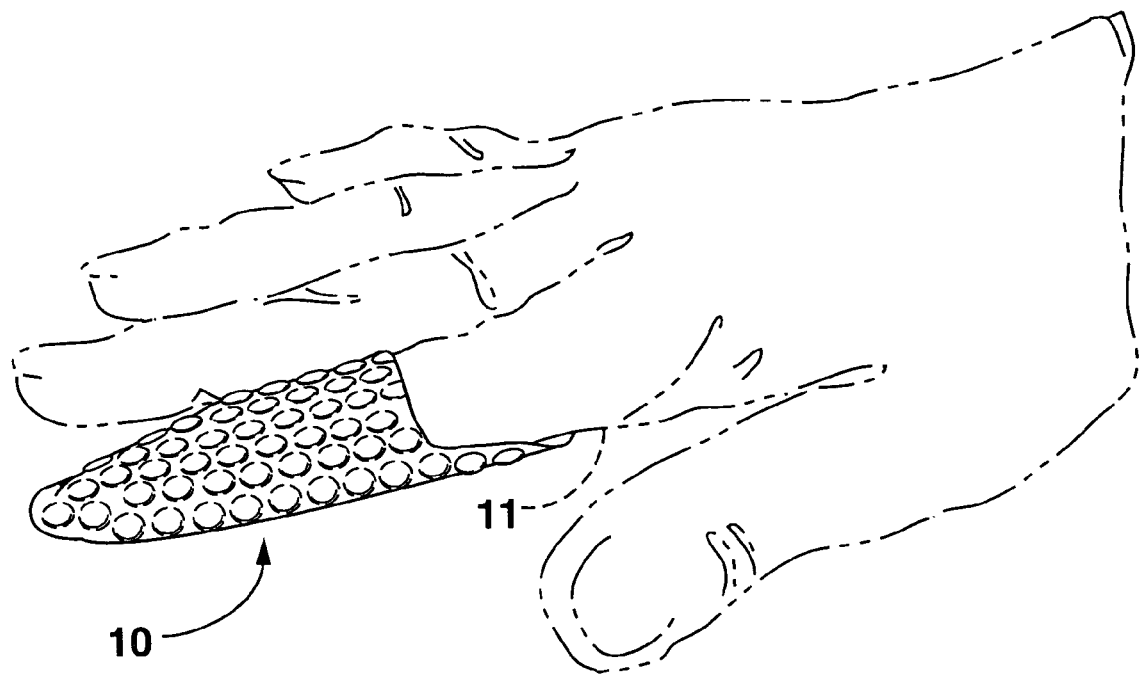
FIG. 1 is a perspective view of a finger wipe on a finger according to one embodiment of the present invention.

Repeat use of reference characters in the present specification and drawings is intended to represent the same or analogous features or elements of the invention.

DETAILED DESCRIPTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used with another embodiment to yield a still further embodiment. Thus, it is intended that the present invention covers such modifications and variations as come within the scope of the appended claims and their equivalents.

Figure 2:
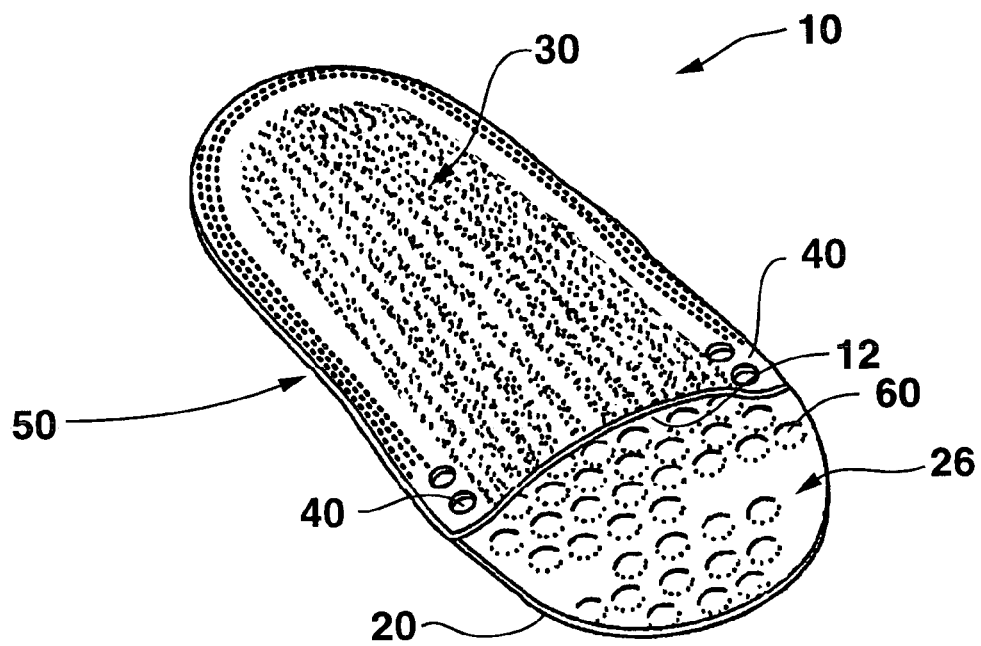
FIG. 2 is a perspective view of a two-sided finger wipe according to one embodiment of the present invention.

An embodiment of a finger cover according to the invention is illustrated as a finger wipe 10 in FIGS. 1 and 2 intended to be placed over a user's finger 11 for cleaning the oral cavity of a person. The finger wipe 10 is made from a first section 20 and a second section 30. The sections may be panels or pieces of the same or a different material, and are bonded or attached together along an edge seam 50 in a finger-shaped pattern so that the bonded sections form a closed end pocket structure with an opening 12 for the insertion of a finger. As discussed in greater detail below, reinforcing welds or bond points 40 may be provided at suitable locations along the seam 50 to enhance the integrity of the seam 50. Once the sections 20 and 30 are bonded or otherwise attached along the seam 50, the materials forming each of the sections 20 and 30 can then be cut adjacent to the seams such that the finger-shaped wipe 10 is formed. In an alternative embodiment, the sections 20 and 30 are cut and bonded in a single processing step.

The seam 50 is formed so as to be relatively pliable and "soft", and does not require additional processing, such as micro-cutting. The seam should not irritate sensitive skin or body parts, and it is not necessary to invert the finger wipe 10 after cutting along the seam 50.

Figure 3:
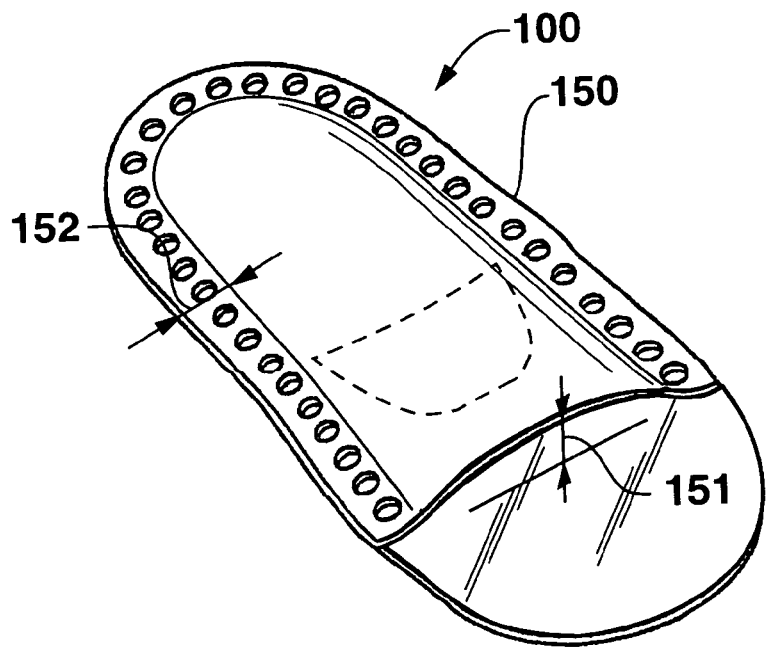
FIG. 3 is a perspective view of a prior art finger wipe having a circumferential seam formed with convention ultrasonic weld points.
Figure 4:
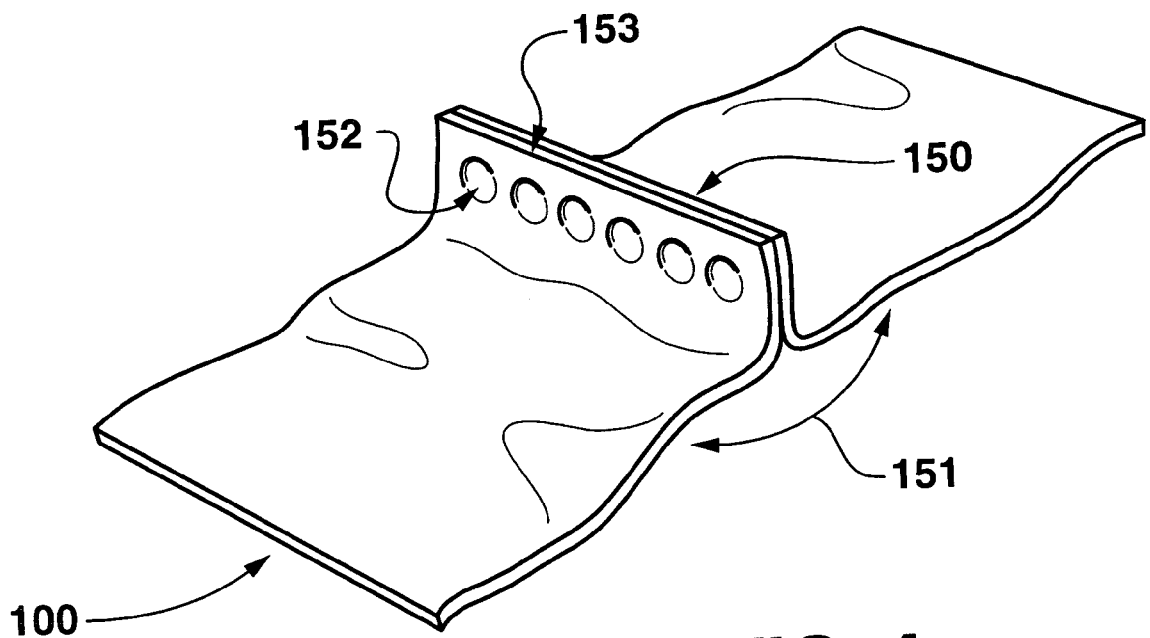
FIG. 4 is an exploded view of a seam portion of a finger wipe and is used to explain principals of the present invention.

FIG. 3 depicts a prior art finger wipe having a seam 150 defined by ultrasonically welded bond points. The seam 150 has an overall width 152 of about 4-5 mm. when the opposed sections are flat (i.e., the angle 151 between the panels is near zero degrees). Referring to FIG. 4, the width 152 becomes a height dimension 153 (in a Z-direction) when the sections are spread apart such that the angle 151 between the panels approaches 180 degrees and the seam 150 is oriented generally perpendicular to the plane of the panels. It should be appreciated that an increased width 152 results in an increased height 153 upon a user donning the finger wipe 10, thus resulting in an increased stiffness of the seam 150.

In accordance with the present invention, the seam 50 around the peripheral edges of the opposed panel sections 20, 30 is carefully formed and defined to be generally flush with the panel sections. In other words, the seam has a minimal width or height with respect to the panel sections. More specifically, the flush seam 50 is generally less than 1 millimeter (mm) in width and 1 mm in height along generally the entire perimeter of the seam 50. In some embodiments, the seam 50 is less than 500 microns in width and 500 microns in height. In some further embodiments, the seam is less than 400 microns in width and 400 microns in height. In still further embodiments, the seam 50 is less than 300 microns in width and 300 microns in height. In some further embodiments, the seam 50 is less than 200 microns in width and 200 microns in height. In yet other embodiments, the seam 50 is less than 100 microns in width and 100 microns in height, and may be less than 50 microns in width and 50 microns in height.

Figure 11:
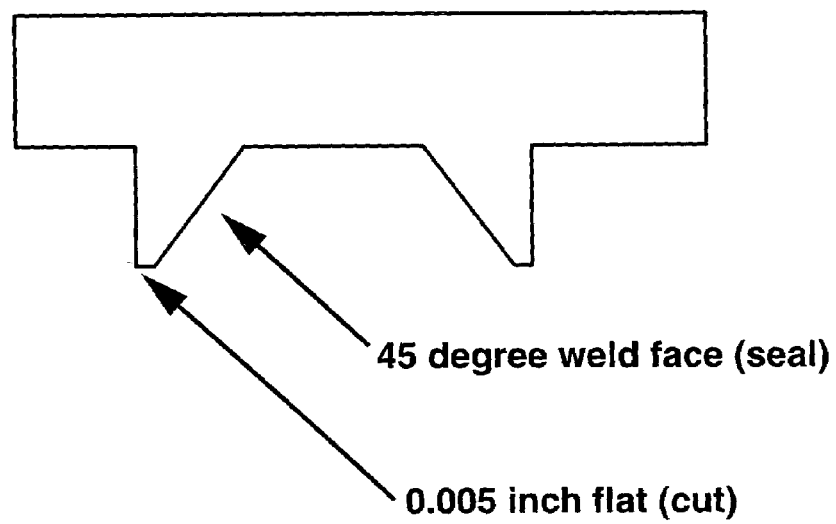
FIG. 11 is a diagrammatic cross-sectional view of a cut/seal horn that may be used to form seams according to the invention.

The seams 50 may be formed by various known techniques, particularly thermal and ultrasonic bonding methods. In a particularly desirable process, the seams 50 are formed by an ultrasonic cut-and-seal process utilizing conventional ultrasonic bonding machines wherein a finger wipe pattern is cut from opposed sheets of materials and the panel sections are sealed in a single processing step. The width and height of the seam is controlled by carefully defining the dimensions and geometry of the bonding horn or bonding anvil, or ultrasonic sewing die. For example, FIG. 11 is a cross-sectional depiction of a bonding horn configured to produce finger wipes having the desired seam characteristics. The horn is configured with the overall shape (planar) of the finger wipe and includes a circumferential cut knife and weld face depicted in FIG. 11. The weld face is defined at a defined angle with respect to the cut knife, which has a cutting edge of desired length. In the illustrated embodiment, the weld face is at an angle of about 45 degrees with respect to the cut knife, and the cut knife has a 5 mil cutting edge. It should be appreciated that these dimensions may vary within the scope and spirit of the invention and various suitable combinations may be readily determined through routine experimentation. This single process cut-and-seal technique is well known to those skilled in the art and a further detailed explanation thereof is not necessary for purposes of the present description.

It may be desired that one or both of the panel sections include a textured surface. A well know method for forming a textured surface in a nonwoven material is a thermal bonding process wherein raised unbonded (or lightly bonded) areas are surrounded by bonded regions. A textured material formed by such a process may be desired as an outer cover layer in finger wipes 10 according to the invention. For example, in the embodiment of FIG. 2, the outer section panel 20 is a thermally bonded material having raised unbonded regions or tufts 60 surrounded by bonded regions.

Figure 8:
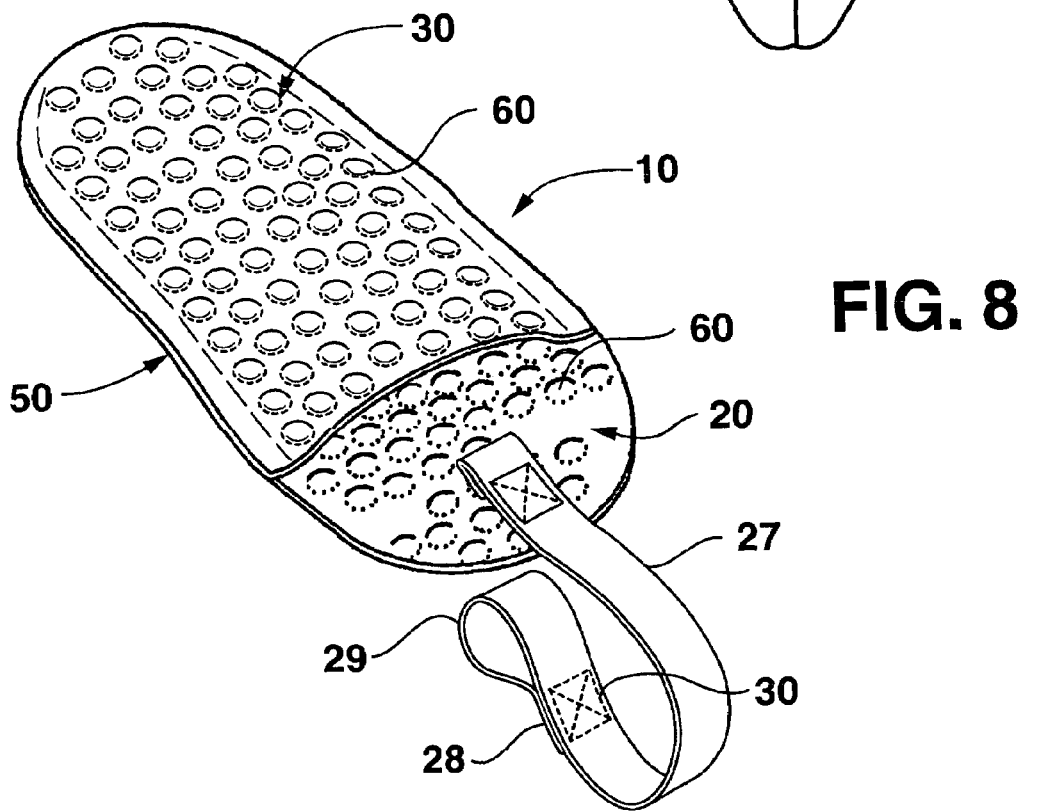
FIG. 8 is a perspective view of another embodiment of a finger wipe made according to the invention.

The stiffness of the seams 50 is also a factor of panel thickness and patterns formed in the panel material. In this regard, it may be desired not to included bonded regions of the point bonded material in the seam 50. In the embodiment of FIG. 8, both panel sections 20, 30 are formed from a thermally point bonded material having a border area or strip of unbonded material along the seam 50 such that the seam 50 is formed between unbonded border regions of the panel members 20, 30. Thus, bonded regions of the materials do not add increased stiffness along the seam 50.

Figure 9:
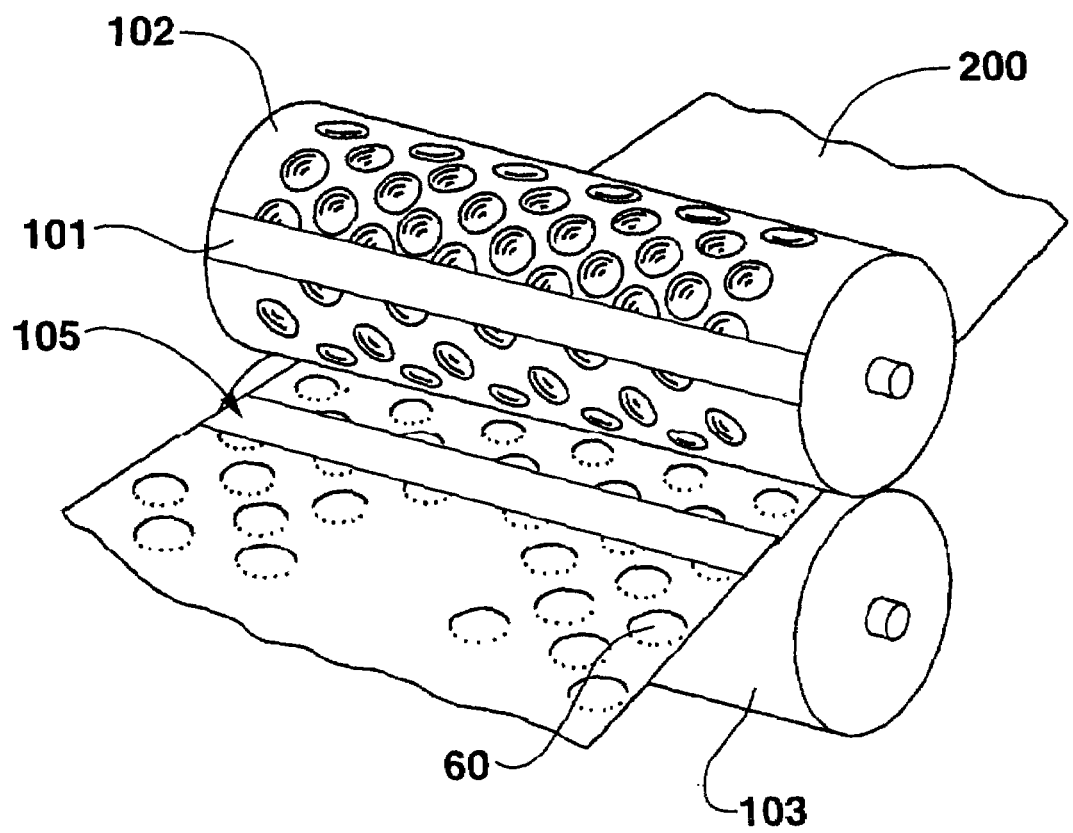
FIG. 9 is an operational view of a method for making a texturized substrate for use in a finger wipe according to the invention.

FIG. 9 graphically depicts a thermal point bonding process that may be useful in producing a material for use in the embodiments of FIGS. 2 and 8. In this process, a nonwoven substrate 200 is fed into the nip between a patterned roll 102 and a smooth roll 103. The unbonded raised portions or tufts 60 are formed in the substrate by the recesses in the patterned roll 102. The roll 102 includes one or more longitudinally extending grooves 101 that produce unpatterned and unbonded regions 105 in the substrate that are spaced apart a distance determined by the circumferential spacing of the grooves 101 on the roll 102 (or diameter of the roll 102 if a single groove 101 is used). The regions 105 may be spaced apart along the substrate 200 a distance about equal to the width of the finger wipes 10 so that the regions 105 define the border regions for forming the seams 50.

To further enhance the strength and integrity of the seam 50 during donning and use of the wipe 10, it may be desired to include additional reinforcing welds or bond points at select locations along the seam 50. For example, in the embodiment of FIG. 2, additional ultrasonic or thermal weld points 40 are provided adjacent to the open unsealed edges of the panel sections 20, 30. These bond points 40 enhance the seam 50 at a location that may tend to separate during donning of the wipe 10. The bond points may be formed by an additional processing step after forming the seam 50.

Figure 5:
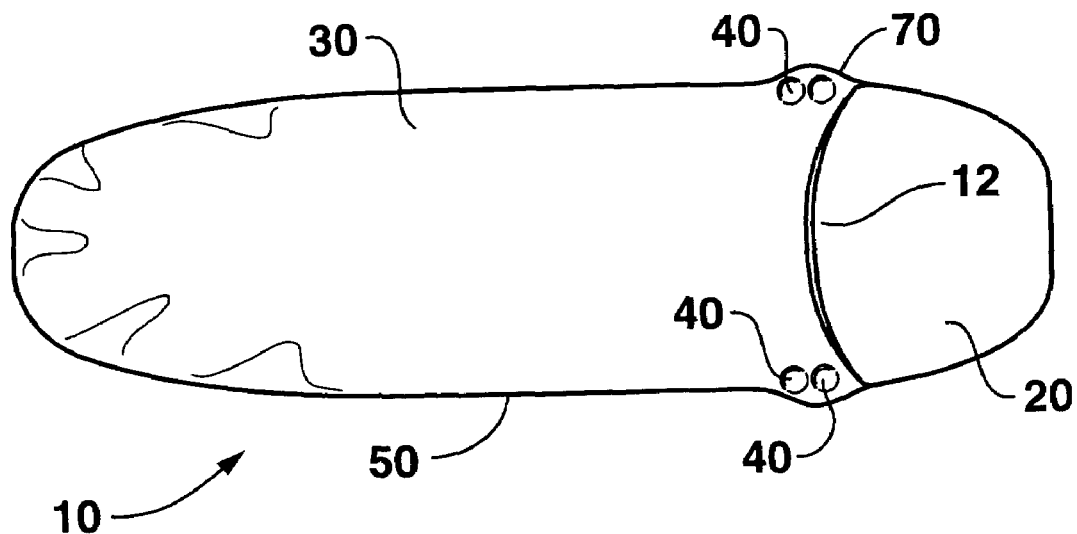
FIG. 5 is a top view of another embodiment of a finger wipe made according to the present invention.

In the embodiment of FIG. 5, the panel sections include laterally oriented extensions adjacent the opening 12. These extensions may be ear-like structures 70 provided at both sides of the opening 12. The structures 70 can be made in any shape, but preferably in a shape that can help the user to place the wipe 10 onto a finger. The size of the ear-like structures 70 desirably does not create stiffness along the seam line 50. Additional weld or bond points 40 may be provided in the area of the ear-like structures 70 to strengthen the seam 50 in these areas. The peripheral outer edges of the structures 70 are to be sealed if the wipes are made in a single cut and seal process. In an alternate embodiment, the flush seam 50 may extend through the structures 70 to the opening 12 with the outer edges of the structures remaining unsealed.

Figure 6:
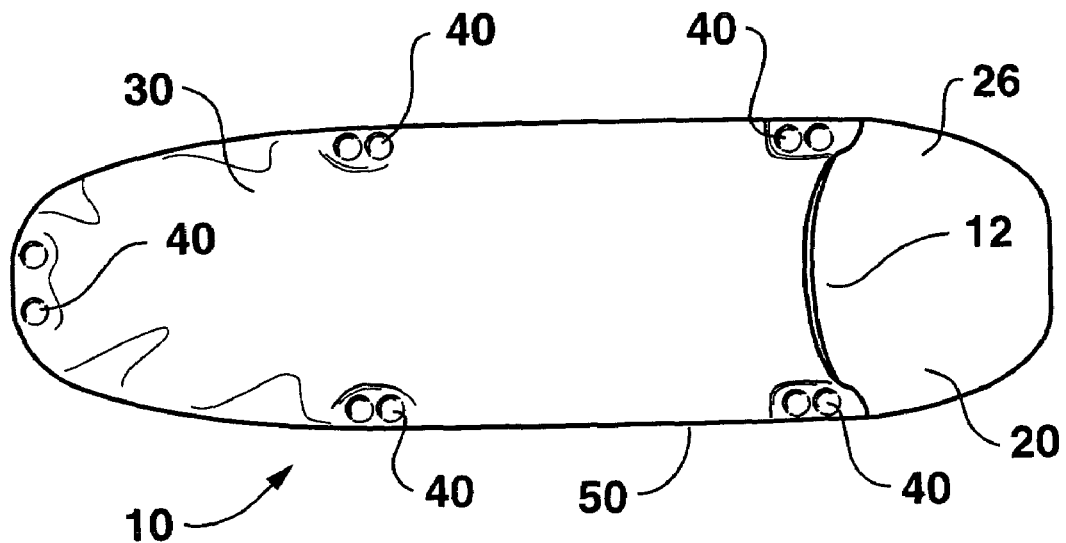
FIG. 6 is a top view of an alternative embodiment of a finger wipe made in accordance with the present invention.

In the embodiment of FIG. 6, groupings of one or more reinforcing bonds 40 are spaced around the perimeter of the seam 50 at any location where addition strength may be needed. The number and frequency of the reinforcing bond points 40 should be selected so as to provide a desired degree of reinforcement without adding appreciable stiffness to the overall seam 50

Figure 7:
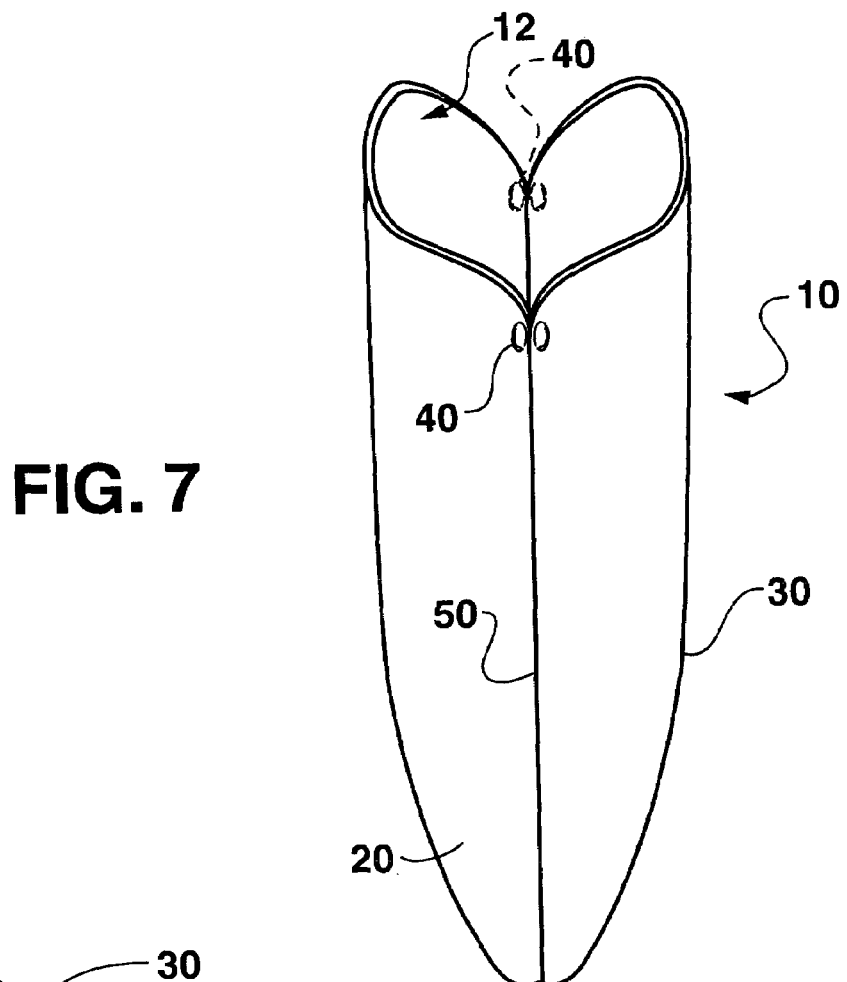
FIG. 7 is a side perspective view of yet another embodiment of a finger wipe according to the present invention.

FIG. 7 depicts an embodiment of a finger wipe 10 wherein the opening 12 is defined by a V-shaped configuration at the ends of the seam 50. This shape may aid a user in opening and donning the wipe 10, but may also define areas of increased stress in the donning process. Additional weld or bond points 40 may be provided along the seam 50 adjacent to the opening 12 to reinforce the seam at the increased stress concentration points.

Referring again to FIG. 2, the first panel section 20 may have a length greater than the second panel section 30 such that the first section 20 includes a longitudinally extending portion 26 that extends beyond the edge of the second section 30. This portion 26 may serve as a "pull-on" tab and can facilitate placement of the finger wipe 10 over the user's finger. It should be appreciated that a pull-on tab or section may be positioned on any suitable portion of the finger wipe 10. For example, a pull-on tab 26 may be provided in the middle portion of the finger wipe 10 so that a user can pull the tab 26 in a direction perpendicular to the lengthwise direction of the wipe 10. As a result, the tab 26 can facilitate insertion of a finger into the wipe 10 by "spreading out" the wipe in an upwardly direction as a finger is inserted therein.

In some embodiments of the present invention, it may also be desirable to provide the finger wipe 10 with an additional fastening means in addition to or alternative to an elastic component. For example, the finger wipe can include a fastening mechanism that attaches to one or more fingers of a user, while the finger wipe is fitted onto another finger. In a particular embodiment illustrated in FIG. 8, the additional fastening mechanism includes a strap or similar attaching structure 27 made of any suitable material and having fastening structure, such as a loop 29, formed in an end thereof. The structure 27 is attached to the wipe 10 using a variety of well known attachment methods, such as thermal, chemical, or mechanical bonding. For example, in one embodiment, the structure 27 is attached to the panel section 20 by an adhesive, or stitching. For most applications, the attaching structure 27 may have a length of from about 1 inch to about 12 inches. In general, the fastening portion 29 can have any shape so as to fit onto one or more of the user's fingers.

The dimensions of finger wipes in accordance with the present invention will depend upon the particular application and purpose for which the finger wipe is to be used. For instance, the finger wipe can be constructed in order to fit around the finger of an adult or the finger of a child. Further, the finger wipe can also be constructed to fit around two fingers. For most single finger wipes, the wipe should have a length of from about 1 inch to about 7 inches and a median flattened width of from about 0.5 inches to about 4 inches. When constructed to fit around two fingers, the finger wipe can have a median width of from about 0.75 inches to about 2.5 inches, depending on the elasticity of the wipe.

Prior to being shipped and sold, the finger wipe of the present invention can be placed in various packaging, if desired. Various packaging materials that can be used include ethylene vinyl alcohol (EVA) films, film foil laminates, metalized films, multi-layered plastic films, and the like.

In general, the finger wipes 10 of the present invention can be formed from a variety of materials. U.S. Pat. No. 6,647,549 incorporated herein by reference describes various suitable materials, and combinations of materials, that may be used for wipes 10 incorporating the unique seam structure of the present invention. Non-limiting examples of suitable materials are described below.

Base Layer

As mentioned, the first panel section 20 and the second panel section 30 are formed from a base web that may include one or more layers of fibrous materials used in the art for making wipes. For example, either or both of the panel sections may comprise a liquid absorbent material or a non-absorbent material. When comprising a liquid absorbent material, the base webs may comprise any suitable fabric material, such as a woven fabric, a nonwoven fabric, or a knitted fabric.

In one embodiment, the base web comprises a spunbond web, a coform web, a tissue web, a meltblown web, a bonded carded web, and laminates thereof. A nonwoven material can be made from various fibers, such as synthetic or natural fibers. For instance, in one embodiment, synthetic fibers, such as fibers made from thermoplastic polymers, can be used to construct the cover layer of the present invention. For example, suitable fibers could include melt-spun filaments, staple fibers, melt-spun multi-component filaments, and the like. These synthetic fibers or filaments used in making the nonwoven material may have any suitable morphology and may include hollow or solid, straight or crimped, single component, conjugate or biconstituent fibers or filaments, and blends or mixtures of such fibers and/or filaments, as are well known in the art.

The synthetic fibers used in the present invention may be formed from a variety of thermoplastic polymers where the term "thermoplastic polymer" refers to a long chain polymer that repeatedly softens when exposed to heat and substantially returns to its original state when cooled to ambient temperature. As used herein, the term "polymer" generally includes, but is not limited to, homopolymers, copolymers, such as for example, block, graft, random, and alternating copolymers, terpolymers, etc., and blends and modifications thereof.

Exemplary thermoplastics include, without limitation, poly(vinyl) chlorides, polyesters, polyamides, polyfluorocarbons, polyolefins, polyurethanes, polystyrenes, poly(vinyl) alcohols, caprolactams, and copolymers of the foregoing, and elastomeric polymers such as elastic polyolefins, copolyether esters, polyamide polyether block copolymers, ethylene vinyl acetates (EVA), block copolymers having the general formula A-B-A' or A-B like copoly(styrene/ethylene-butylene), styrene-poly(ethylene-propylene)-styrene, styrene-poly(ethylene-butylene)-styrene, (polystyrene/poly(ethylene-butylene)/polystyrene, poly(styrene/ethylene-butylene/styrene), A-B-A-B tetrablock copolymers and the like.

Many polyolefins are available for fiber production, for example polyethylenes such as Dow Chemical's PE XU 61800.41 linear low-density polyethylene ("LLDPE") and 25355 and 12350 high-density polyethylene ("HDPE") are such suitable polymers. Fiber-forming polypropylenes include Exxon Chemical Company's Escorene® PD 3445 polypropylene and Montell Chemical Co.'s PF-304 and PF-015. Many other polyolefins are commercially available and include polybutylenes and others.

Synthetic fibers added to the nonwoven web can also include staple fibers that can be added to increase the strength, bulk, softness and smoothness of the base sheet. Staple fibers can include, for instance, various polyolefin fibers, polyester fibers, nylon fibers, polyvinyl acetate fibers, cotton fibers, rayon fibers, non-woody plant fibers, and mixtures thereof.

Besides, or in addition to, synthetic fibers, pulp fibers can also be used to construct the cover layer. The pulp fibers used in forming the cover layer may be soft wood fibers having an average fiber length of greater than 1 mm, and particularly from about 2 to 5 mm based on a length weighted average. Such fibers can include northern softwood kraft fibers, redwood fibers, and pine fibers. Secondary fibers obtained from recycled materials may also be used. In addition, hardwood pulp fibers, such as eucalyptus fibers, or thermomechanical pulp can also be utilized in the present invention.

In some embodiments of the present invention, the base web can include a hydraulically entangled web (or hydroentangled). Hydroentangled webs, which are also known as spunlace webs, refer to webs that have been subjected to columnar jets of a fluid that cause the fibers in the web to entangle. For example, in one embodiment, the cover layer can comprise HYDROKNIT®, a nonwoven composite fabric that contains 70% by weight pulp fibers that are hydraulically entangled into a continuous filament material. HYDROKNIT® material is commercially available from Kimberly-Clark Corporation of Neenah, Wis. Hydraulic entangling may be accomplished utilizing conventional hydraulic entangling equipment such as may be found in, for example, U.S. Pat. No. 3,485,706 to Evans or U.S. Pat. No. 5,389,202 to Everhart, et al., the disclosures of which are hereby incorporated by reference.

In one embodiment, the base web may comprise a laminate containing two or more webs. For instance, the web may comprise a spunbonded/meltblown/spunbonded laminate, a spunbonded/meltblown laminate and the like.

For nonwoven webs containing substantial amounts of synthetic fibers, the webs may be bonded or otherwise consolidated in order to improve the strength of the web. Various methods may be utilized in bonding webs of the present invention. Such methods include through air bonding and thermal point bonding as described in U.S. Pat. No. 3,855,046 to Hansen, et al. which is incorporated herein by reference. In addition, other conventional means of bonding, such as oven bonding, ultrasonic bonding, hydroentangling, or combinations of such techniques, may be utilized in certain instances.

In one embodiment, thermal point bonding is used which bonds the fibers together according to a pattern. In general, the bonding areas for thermal point bonding, whether pattern unbonded or pattern bonded fabrics, can be in the range of 50% total bond area or less. More specifically, the bond areas of the present inventive webs can be in the range of from about 60% to about 10% total bond area.

When the finger wipe of the present invention is used to scrub adjacent surfaces or is to be used in dental applications, in some embodiments, the cover layer may include a texturized surface such as the surface illustrated in the embodiments shown in FIGS. 1, 2, and 8. When used in dental applications, for instance, the texturized surface can facilitate removal of residue and film from the teeth and gums.

The manner in which a texturized surface is formed on a nonwoven web for use in the present invention can vary depending upon the particular application of the desired result. In the embodiment shown in FIG. 8, the panel sections are made from a nonwoven web that has been thermally point unbonded to form a plurality of tufts 60. As used herein, a substrate that has been "thermally point unbonded" refers to a substrate that includes raised unbonded areas or lightly bonded areas that are surrounded by bonded regions. For example, as shown in the figures, the tufts 60 are the unbonded or lightly bonded areas that form raised projections off the surface of the nonwoven web to provide the necessary texture.

The substrate used to produce the point unbonded material can vary depending upon the particular application. For instance, the substrate can be a single layer or can include multiple layers of material. For most applications, the total basis weight of the substrate should be at least 1 osy, and particularly from about 3 osy to about 9 osy. Higher basis weights are needed in order to produce tufts 60 with an appropriate height.

For most applications, the substrate should also include at least one nonwoven layer that has a high bulk to mass ratio. Examples of materials having high bulk include through air bonded nonwoven webs made from polymeric fibers and filaments. The nonwoven webs can be made from crimped polymeric fibers and filaments and/or from fibers and filaments having a shaped cross-sectional profile. For example, crimped bicomponent polyethylene/polypropylene fibers can be used. Shaped fibers include pentalobal fibers and hollow fibers.

Besides thermal bonding, ultrasonic bonding can also be used to produce the point unbonded material, as in known to those skilled in the art.

The point unbonded material contains tufts having a height of at least 0.02 inches. More particularly, the height of the tufts will vary from about 0.05 inches to about 0.1 inches. As shown in FIG. 8, the tufts 60 can have a circular shape. It should be understood, however, that tufts 60 can have any suitable shape. For instance, the tufts can be square, triangular, or even in the shape of a doughnut. The may be uniformly applied over one or both panels of the finger wipe. In other embodiments, however, the tufts may be arranged in a pattern. For example, in other embodiments, the tufts may be arranged in a circular pattern, a spiral pattern, or in any other suitable pattern. Such a pattern may assist in scrubbing an adjacent surface with the finger wipe.

The total bond area surrounding the tufts can also vary depending upon the particular application. For most embodiments, the bond area surrounding the tufts can be from about 15% to about 60% of the surface area of the material, and particularly from about 20% to about 40% of the surface area of the material.

Besides point unbonded materials, there are many other methods for creating texturized surfaces on base webs and many other texturized materials can be utilized.

Examples of known nonwoven, texturized materials, include rush transfer materials, flocked materials, wire-formed nonwovens, and the like. Moreover, through-air bonded fibers, such as through-air bonded bicomponent spunbond, or point unbonded materials, such as point unbonded spunbond fibers, can be incorporated into the base web to provide texture to the wipe.

Textured webs having projections from about 0.1 mm to about 25 mm, such as pinform meltblown or wireform meltblown, can also be utilized in a base web of the present invention. Still another example of suitable materials for a texturized base web includes textured coform materials. In general, "coform" means a process in which at least one meltblown diehead is arranged near a chute through which other materials are added to the web while it forms. Such other materials can include, for example, pulp, superabsorbent particles, or cellulose or staple fibers. Coform processes are described in U.S. Pat. No. 4,818,464 to Lau and U.S. Pat. No. 4,100,324 to Anderson, et al. Webs produced by the coform process are generally referred to as coform materials.

Figure 10:
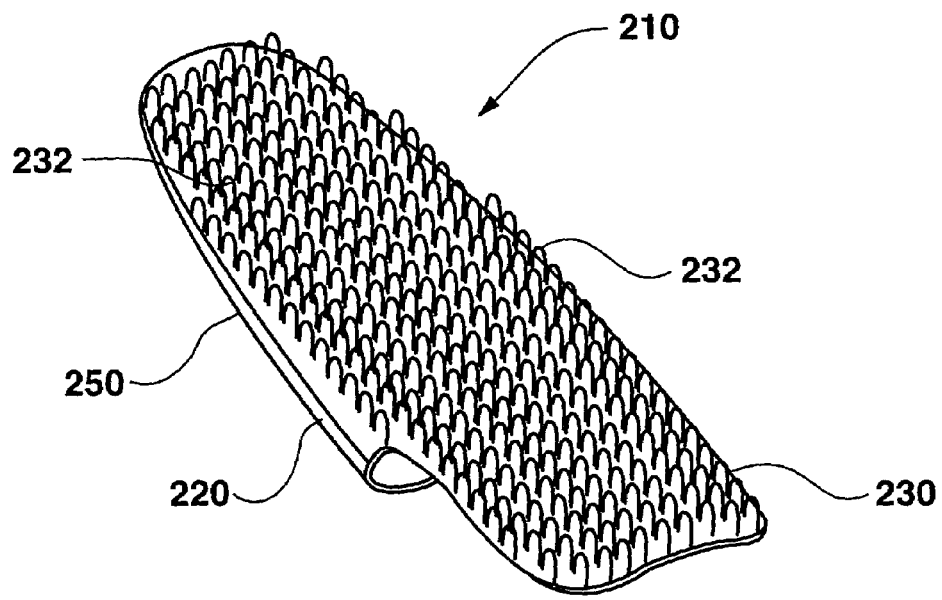
FIG. 10 is a perspective view of another embodiment of a finger wipe having a loop texturized surface.

In one embodiment, the texturized material can be a loop material. As used herein, a loop material refers to a material that has a surface that is at least partially covered by looped bristles. For instance, referring to FIG. 10, an embodiment of a finger wipe generally 210 is shown that incorporates a loop material. In particular, the finger wipe 210 includes a first panel 220 and a second panel 230. The second panel 230 incorporates looped bristles 232. The bristles 232 may be provided on a separate layer that is laminated onto a suitable base web layer, or be incorporated with a single layer base material. The looped bristles 232 can vary depending upon the particular application. For instance, the stiffness of the looped bristles is varied by varying different factors, including the height of the loop, the inherent properties of the looped material, the fiber diameter, the fiber type, and any post-formation treatments ((e.g.) chemical coatings) that may be performed on the looped material. Further, the looped bristles can be sparsely spaced apart or can be densely packed together.

The loop material can be made in a number of different ways. For example, the loop can be a woven fabric or a knitted fabric. In one embodiment, the loop material is made by needle punching loops into a substrate. In other embodiments, the loop material can be formed through a hydroentangling process or can be molded, such as through an injection molding process. Of course, any other suitable technique known in the art for producing looped bristles can also be used.

In one particular embodiment of the present invention, the loop material used in the finger wipe is a loop material commonly used in hook and loop fasteners. For example, VELCRO loops No. 002 made by VELCRO, USA, Inc. can be used. This material is made with nylon loops. In an alternative embodiment, the looped fastener material can be elastic. Elastic woven loop materials include VELSTRETCH Tape 9999 and MEDFLEX Tape 9399, both marketed by VELCRO, USA, Inc.

Liquid Impermeable Layer

Finger wipes according to the invention may include a liquid impermeable layer that is positioned interior of the wipe adjacent one or both of the panel sections. This liquid impermeable layer may be separate from the base web, or constitute a component of the base web.

In one embodiment, the liquid impermeable layer can be made from liquid-impermeable plastic films, such as polyethylene and polypropylene films. Generally, such plastic films are impermeable to gases and water vapor, as well as liquids.

While completely liquid-impermeable films can prevent the migration of liquid from outside the wipe to the finger, the use of such liquid- and vapor-impermeable barriers can sometimes result in a relatively uncomfortable level of humidity being maintained in the finger wipe. As such, in some embodiments, breathable, liquid-impermeable barriers are desired. As used herein, the term "breathable" means that the barrier or film is pervious to water vapor and gases. In other words, "breathable barriers" and "breathable films" allow water vapor and gases to pass therethrough, but not necessarily liquids.

For instance some suitable breathable, liquid-impermeable barriers can include barriers such as disclosed in U.S. Pat. No. 4,828,556 to Braun, et al., which is incorporated herein in its entirety by reference. The breathable barrier of Braun, et al. is a multilayered, clothlike barrier comprised of at least three layers. The first layer is a porous nonwoven web; the second layer, which is joined to one side of the first layer, comprises a continuous film of PVOH; and the third layer, which is joined to either the second layer or the other side of the first layer not joined with the second layer, comprises another porous nonwoven web. The second layer continuous film of PVOH is not microporous, meaning that it is substantially free of voids that connect the upper and lower surfaces of the film.

In other cases, various films can be constructed with micropores therein to provide breathability. The micropores form what is often referred to as tortuous pathways through the film. Liquid contacting one side of the film does not have a direct passage through the film. Instead, a network of microporous channels in the film prevents water from passing, but allows water vapor to pass.

In some instances, the breathable, liquid-impermeable barriers are made from polymer films that contain any suitable substance, such as calcium carbonate. The films are made breathable by stretching the filled films to create the microporous passageways as the polymer breaks away from the calcium carbonate during stretching. In some embodiments, the breathable film layers can be used in thicknesses of from about 0.01 mils to about 5 mils, and in other embodiments, from about 0.01 mils to about 1.0 mils.

An example of a breathable, yet fluid penetration-resistant material is described in U.S. Pat. No. 5,591,510 to Junker, et al., which is incorporated herein by reference. The fabric material described in Junker, et al. contains a breathable outer layer of paper stock and a layer of breathable, fluid-resistant nonwoven material. The fabric also includes a thermoplastic film having a plurality of perforations which allow the film to be breathable while resisting direct flow of liquid therethrough.

In addition to the films mentioned above, various other breathable films can be utilized in the present invention. One type of film that may be used is a nonporous, continuous film, which, because of its molecular structure, is capable of forming a vapor-permeable barrier. Among the various polymeric films which fall into this type include films made from a sufficient amount of poly(vinyl alcohol), polyvinyl acetate, ethylene vinyl alcohol, polyurethane, ethylene methyl acrylate, and ethylene methyl acrylic acid to make them breathable. It is believed that films made from such polymers solubilize water molecules and allow transportation of those molecules from one surface of the film to the other. Accordingly, such films may be sufficiently continuous, i.e., nonporous, to make them liquid-impermeable but still allow for vapor permeability.

Still, other breathable, liquid-impermeable barriers that can be used in the present invention are disclosed in U.S. patent application Ser. No. 08/928,787 entitled "Breathable, Liquid-impermeable, Apertured Film/Nonwoven Laminate and Process for Making the Same", which is incorporated herein in its entirety by reference. For example, breathable films and/or apertured films can be utilized in the present invention. Such films can be made within a laminate structure. In one embodiment, a breathable, liquid-impermeable, apertured film/nonwoven laminate material can be formed from a nonwoven layer, an apertured film layer, and a breathable film layer. The layers may be arranged so that the apertured film layer or the breathable film layer is attached to the nonwoven layer.

For instance, in one embodiment, an apertured film can be used in the present invention that is made from any thermoplastic film, including polyethylene, polypropylene, copolymers of polypropylene or polyethylene, or calcium carbonate-filled films. The particular aperturing techniques utilized to obtain the apertured film layer may be varied. The film may be formed as an apertured film or may be formed as a continuous, non-apertured film and then subjected to a mechanical aperturing process.

Liquid impermeable layers, as described above, can be used alone or incorporated into a laminate when used to construct the finger wipe of the present invention. When incorporated into a laminate, the laminate can include various nonwoven webs in combination with the liquid impermeable layer. For instance, liquid impermeable laminates can be formed from many processes, such as, meltblowing processes, spunbonding processes, coforming processes, spunbonding/meltblowing/spunbonding processes (SMS), spunbonding/meltblowing processes (SM), and bonded carded web processes. For instance, in one embodiment, the nonwoven layer of a laminate liquid impermeable layer of the present invention is a spunbond/meltblown/spunbond (SMS) and/or spunbond/meltblown (SM) material. An SMS material is described in U.S. Pat. No. 4,041,203 to Brock, et al. which is incorporated herein in its entirety by reference. Other SMS products and processes are described for example in U.S. Pat. No. 5,464,688 to Timmons, et al., U.S. Pat. No. 5,169,706 to Collier, et al. and U.S. Pat. No. 4,766,029 to Brock, et al., all of which are also incorporated herein in their entireties by reference. Generally, an SMS material will contain a meltblown web sandwiched between two exterior spunbond webs. Such SMS laminates are available from Kimberly-Clark Corporation under marks such as Spunguard® and Evolution®. The spunbonded layers on the SMS laminates provide durability and the internal meltblown barrier layer provides porosity and additional clothlike feel. Similar to an SMS laminate, an SM laminate is a spunbond layer laminated to a meltblown layer.

In forming a finger wipe of the present invention with a liquid impermeable layer, the layer can be bonded together with the other layers of the wipe in a number of various ways. Thermal bonding, adhesive bonding, ultrasonic bonding, extrusion coating, and the like, are merely examples of various bonding techniques that may be utilized in the present process to attach the liquid impermeable layer to the fibrous layers of the finger wipe.

In some embodiments, any of the above layers and/or materials can also be dyed or colored so as to form a base web or liquid impermeable layer having a particular color. For example, in one embodiment, the liquid impermeable layer can be provided with a colored background.

Elastic Component

As described above, the finger wipes 10 may include one or more elastic components for providing the wipe with form-fitting properties. For example, one or both of the panel sections may be made of an elastic material, or include elastic components. For instance, either or both panels can contain elastic strands or sections uniformly or randomly distributed throughout the material. Alternatively, the elastic component can be an elastic film or an elastic nonwoven web.

In general, any material known in the art to possess elastomeric characteristics can be used in the present invention as an elastomeric component. Useful elastomeric materials can include, but are not limited to, films, foams, nonwoven materials, etc. For example, suitable elastomeric resins include block copolymers having the general formula A-B-A' or A-B, where A and A' are each a thermoplastic polymer endblock which contains a styrenic moiety such as a poly(vinyl arene) and where B is an elastomeric polymer midblock such as a conjugated diene or a lower alkene polymer. Block copolymers for the A and A' blocks, and the present block copolymers are intended to embrace linear, branched and radial block copolymers. In this regard, the radial block copolymers may be designated (A-B)m-X, wherein X is a polyfunctional atom or molecule and in which each (A-B)m- radiates from X in a way that A is an endblock. In the radial block copolymer, X may be an organic or inorganic polyfunctional atom or molecule and m is an integer having the same value as the functional group originally present in X. It is usually at least 3, and is frequently 4 or 5, but not limited thereto. Thus, in the present invention, the expression "block copolymer," and particularly "A-B-A" and "A-B" block copolymer, is intended to embrace all block copolymers having such rubbery blocks and thermoplastic blocks as discussed above, which can be extruded (e.g., by meltblowing), and without limitation as to the number of blocks. The elastomeric nonwoven web may be formed from, for example, elastomeric (polystyrene/poly(ethylene-butylene)/polystyrene) block copolymers. Commercial examples of such elastomeric copolymers are, for example, those known as KRATON® materials which are available from Shell Chemical Company of Houston, Tex. KRATON® block copolymers are available in several different formulations, a number of which are identified in U.S. Pat. Nos. 4,663,220; 4,323,534; 4,834,738; 5,093,422; and 5,304,599, hereby incorporated by reference.

Polymers composed of an elastomeric A-B-A-B tetrablock copolymer may also be used in the practice of this invention. Such polymers are discussed in U.S. Pat. No. 5,332,613 to Taylor, et al. In such polymers, A is a thermoplastic polymer block and B is an isoprene monomer unit hydrogenated to substantially a poly(ethylene-propylene) monomer unit. An example of such a tetrablock copolymer is a styrene-poly (ethylene-propylene)-styrene-poly(ethylene-propylene) or SEPSEP elastomeric block copolymer available from the Shell Chemical Company of Houston, Tex. under the trade designation KRATON® G-1657.

Other exemplary elastomeric materials which may be used include polyurethane elastomeric materials such as, for example, those available under the trademark ESTANE® from B.F. Goodrich & Co. or MORTHANE® from Morton Thiokol Corp., polyester elastomeric materials such as, for example, those available under the trade designation HYTREL® from E.I. DuPont De Nemours & Company, and those known as ARNITEL®, formerly available from Akzo Plastics of Amhem, Holland and now available from DSM of Sittard, Holland.

Another suitable material is a polyester block amide copolymer. Elastomeric polymers can also include copolymers of ethylene and at least one vinyl monomer such as, for example, vinyl acetates, unsaturated aliphatic monocarboxylic acids, and esters of such monocarboxylic acids. The elastomeric copolymers and formation of elastomeric nonwoven webs from those elastomeric copolymers are disclosed in, for example, U.S. Pat. No. 4,803,117.

When incorporating an elastomeric component, such as described above, into a base web of the present invention, it is often desired that the elastomeric material form an elastic laminate with one or more other layers, such as foams, films, apertured films, and/or nonwoven webs. The elastic laminate generally contains layers that can be bonded together so that at least one of the layers has the characteristics of an elastic polymer. Examples of elastic laminates include, but are not limited to, stretch-bonded laminates and neck-bonded laminates.

The elastic member used in neck-bonded materials, stretch-bonded materials, stretch-bonded laminates, neck-bonded laminates and in other similar laminates can be made from materials, such as described above, that are formed into films, such as a microporous film, fibrous webs, such as a web made from meltblown fibers, spunbond filaments or foams. A film, for example, can be formed by extruding a filled elastomeric polymer and subsequently stretching it to render it microporous.

In one embodiment, the elastic member can be a neck stretched bonded laminate. As used herein, a neck stretched bonded laminate is defined as a laminate made from the combination of a neck-bonded laminate and a stretch-bonded laminate. Examples of necked stretched bonded laminates are disclosed in U.S. Pat. Nos. 5,114,781 and 5,116,662, which are both incorporated herein by reference. Of particular advantage, a neck stretch bonded laminate is stretchable in the machine direction and in a cross machine direction. Further, a neck stretch-bonded laminate can be made with a nonwoven basing that is texturized. In particular, the neck stretched bonded laminate can be made so as to include a nonwoven facing that gathers and becomes bunched so as to form a textured surface. In this manner, the neck stretched bonded laminate can be used to form the entire finger wipe having stretch characteristics in two directions and having a textured surface for cleaning the teeth and gums of a user.

Additives

In general, a finger wipe can also be applied with a variety of chemical additives. For instance, any material, chemical, or additive commonly applied by cotton ball, swabs, or gauzes can be applied to a finger wipe of the present invention. Examples of such additives can include, but are not limited to, medications, diaper rash ointments, alcohols, oral anesthetics, facial make-up removal agents, and the like.

In addition, various other additives, chemicals, and materials can be applied to a finger wipe of the present invention. For instance, certain additives can be when the finger wipe is used as an oral cleaning device. For example, in one embodiment, cationic polymers can be coated onto the finger wipe. Cationic polymers can help clean teeth and/or gums because they typically have a strong attraction for negatively charged bacteria and deleterious acidic byproducts that accumulate in plaque. One example of a cationic polymer that is suitable for use in the present invention is chitosan (poly-N-acetylglucosamine, a derivative of chitin) or chitosan salts. Chitosan and its salts are natural biopolymers that can have both hemostatic and bacteriostatic properties. As a result, chitosan can help reduce bleeding, reduce plaque, and reduce gingivitis.

In addition to chitosan and chitosan salts, any other cationic polymer known in the art can generally be applied to a finger wipe of the present invention. For example, in one embodiment, cationic starches are used in the present invention. One such suitable cationic starch is, for example, COBOND, which can be obtained from National Starch. In another embodiment, cationic materials that are oligomeric compounds can be used. In some embodiments, combinations of cationic materials can be utilized.

In addition to the chemical additives mentioned above, a variety of other additives can be applied to a finger wipe of the present invention. For instance, other well known dental agents can be utilized. Examples of such dental agents include, but are not limited to alginates, soluble calcium salts, phosphates, flourides, such as sodium flouride (NaF) or stannous flouride (SnF 2), and the like. Moreover, mint oils and mint oil mixtures can be applied to a finger wipe of the present invention. For instance, in one embodiment, peppermint oil can be applied to the finger wipe. Moreover, in another embodiment, a mint oil/ethanol mixture can be applied. Components of mint oil (e.g., menthol, carvone) can also be used. Additionally, various whitening agents can be applied to the finger wipe. Examples of whitening agents include peroxides and in situ sources of peroxide, such as carbamide peroxide.

Furthermore, in some embodiments, the finger wipe can also comprise an anti-ulcer component. In particular, one embodiment of the present invention can comprise a component designed to act as an anti-*H. pylori* agent. In general, any additive known in the art to be an anti-ulcer or anti-*H. pylori* agent can be used in the present invention. In one embodiment, for example, bismuth salts can be utilized. One particularly effective bismuth salt, bismuth subcitrate, is described in more detail in U.S. Pat. No. 5,834,002 to Athanikar, which is incorporated herein in its entirety by reference thereto. Another example of a suitable bismuth salt is PEPTO-BISMOL sold by The Procter & Gamble Company, containing bismuth subsalicylate. In addition to bismuth salts, other examples of suitable anti-ulcer additives include, but are not limited to, tetracycline, erythromycin, clorithromycin or other antibiotics. Furthermore, any additive useful for treating peptic ulcers, such as H2-blockers, omeprazole, sucralfate, and metronidazole, can be used as well.

Besides the additives mentioned above, other additives can also be applied to the wipe. Such materials can include, but are not limited to, flavoring agents, anti-microbial agents, preservatives, polishing agents, hemostatic agents, surfactants, etc. Examples of suitable flavoring agents include various sugars, breath freshening agents, and artificial sweeteners as well as natural flavorants, such as cinnamon, vanilla and citrus. Moreover, in one embodiment, xylitol, which provides a cooling effect upon dissolution in the mouth and is anti-cariogenic, can be used as the flavoring agent. As stated, preservatives, such as methyl benzoate or methyl paraben, can also be applied to a finger wipe of the present invention. The additives can be applied to the finger wipe as is or they can be encapsulated in order to preserve the additives and/or to provide the additive with time release properties.

In general, the chemical additives described above can be applied to a finger wipe of the present invention according to a number of ways known in the art. For example, the additives can be applied to the wipe using a saturant system, such as disclosed in U.S. Pat. No. 5,486,381 to Cleveland et al., which is incorporated herein by reference. Moreover, the additives can also be applied by print, roll, blade, spray, spray-drying, foam, brush treating applications, etc., which are all well known in the art.

The additives can further be applied as a mixture of molten solids or co-extruded onto the wipe. Additionally, in another embodiment, the chemical additives can be impregnated into the material during manufacturing as is well known in the art. It should be understood that when coated onto a wipe as described above, the additives can be applied to the base web before or after the base web is stamped or bonded to form a finger wipe of the present invention. Furthermore, it should also be understood that, if desired, various additives, solutions, and chemicals can be applied by the consumer to the wipe just before use.

In another embodiment, the additive is encapsulated and then applied to the finger wipe. Encapsulation is a process by which a material or mixture of materials is coated with or entrapped within another material or mixture of materials. The technique is commonly used in the food and pharmaceutical industries. The material that is coated or entrapped is normally a liquid, although it can also be a solid or gas, and is referred to herein as the core material. The material that forms the coating is referred to as the carrier material. A variety of encapsulation techniques are well-known in the art and can be used in the current invention, including spray drying, spray chilling and cooling, coacervation, fluidized bed coating, liposome entrapment, rotational suspension separation, and extrusion.

Regardless of the mechanism utilized to apply the chemical additives to the wipe, the additives can be applied to the wipe via an aqueous solution, non-aqueous solution, oil, lotion, cream, suspension, gel, etc. When utilized, an aqueous solution can contain any of a variety of liquids, such as various solvents and/or water. Moreover, the solution can often contain more than one additive. In some embodiments, the additives applied by an aqueous solution or otherwise constitute approximately less than 80% by weight of the finger wipe. In other embodiments, the additives can be applied in an amount less than about 50% of the weight of the wipe.

EXAMPLES

Various finger wipes were made according to the present invention and tested. In particular, various ones of the Examples described in U.S. Pat. No. 6,647,549 (incorporated herein by reference) were made with seam structures in accordance with the present invention. The finger wipes were constructed from various respective Example materials using ultrasonic welding to form flush seams in a single cut/seal step. The cut and seal horn had a cut knife edge of about 130 microns with the angle between the cut knife and welding area at about 45 degrees. The finger wipes were made with an open end for the insertion of a finger and a closed end. After being formed, the finger wipes had a length of from 1.0 inches to 3.0 inches. The width at the opening normally ranged from 0.6 inches to 1.0 inches (internal diameter). When containing a pull-on tab, the length of the tab ranged from 0.2 to 0.8 inches.

The present applicants believe that a suitable seam structure may be formed with any of the materials used in the Examples of the '549 patent with a seam width of not more than about 1 mm. As the size of the seam structure is reduced, the strength of the seam becomes a factor of the type of material used to make the wipe panels. It is within the purview of those skilled in the art to choose a suitable combination of materials to achieve a desired seam strength and size.

Figure 12:
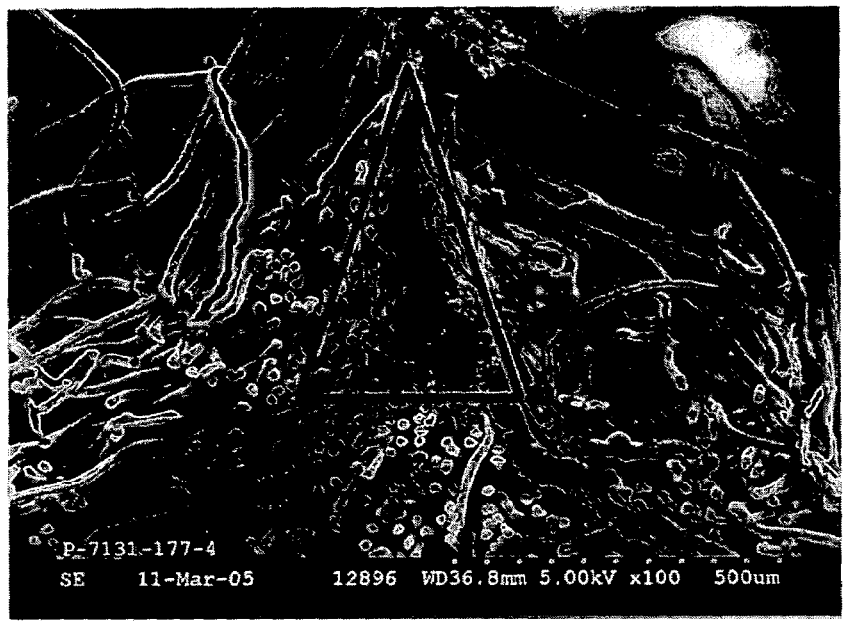
FIG. 12 is a photomicrograph of a seam formed between necked bonded laminates (NBL) sheets particularly showing the microstructure of the seam and fiber structure.

FIG. 12 is a photomicrograph of a cut structure made in a sheet of neck-bonded laminate (NBL) material made with a cut and seal horn having a knife edge of about 130 microns and weld area at a 45 degree angle with respect to the knife edge. The picture particularly illustrates the gradient decline in thickness of the cut towards the cut edge. The NBL sheet was formed by adhesively bonding a polyurethane film of about 0.3 OSY between a pair of opposing polypropylene spunbond facings having a basis weight of about 0.5 osy prior to being stretched or necked. The spunbond facings were necked to a width corresponding to about 30% of their original width.

Figure 13A:
FIGS. 13A and 13B are photomicrographs of material seams made in accordance with aspects of the invention.

FIG. 13A is a photomicrograph of a seam structure between a point-unbonded (PUB) material sheet and an NBL sheet as described above. The PUB material was spunbond polypropylene. The seam was formed by cutting and sealing the materials with the same cut and seal horn described above with respect to FIG. 12. The resulting seam had a seam width of about 0.357 mm.

Figure 13B:
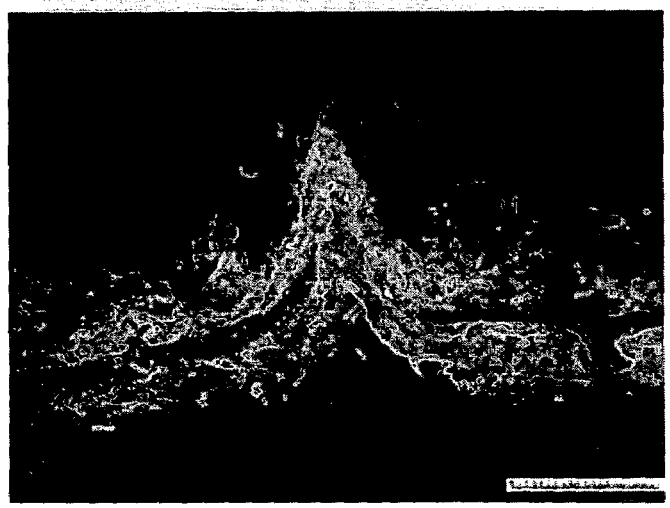

FIG. 13B is a photomicrograph of a seam structure between two NBL sheets as described above with respect to claim FIG. 12. The resulting seam structure was significantly less than 1 mm.

Although various embodiments of the invention have been described using specific terms, devices, and methods, such description is for illustrative purposes only. The words used are words of description rather than of limitation. It is to be understood that changes and variations may be made by those of ordinary skill in the art without departing from the spirit or scope of the present invention, which is set forth in the following claims. In addition, it should be understood that aspects of the various embodiments may be interchanged both in whole or in part. Therefore, the spirit and scope of the appended claims should not be limited to the description of the preferred versions contained therein.

What is claimed is:

1. A finger cover comprising:
   a tubular structure having an open end for the insertion of a finger, said tubular structure comprising a first panel attached to a second panel along an outwardly facing circumferential edge seam, said seam being less than about 1 millimeter (mm) in width and about 1 mm in height generally along the length thereof;
   reinforcement weld points defined at at least one selected location along said seam to reinforce said seam at said location;
   wherein said reinforcement weld points are disposed at locations adjacent said open end of said tubular structure; and
   wherein said panel members comprise lateral extensions adjacent said open end of said tubular structure, said reinforcement weld points defined in said extensions.

2. The finger cover as in claim 1, wherein said seam is less than about 500 microns in width and about 500 microns in height.

3. The finger cover as in claim 1, wherein said seam is less than about 400 microns in width and about 400 microns in height.

4. The finger cover as in claim 1, wherein said seam is less than about 300 microns in width and about 300 microns in height.

5. The finger cover as in claim 1, wherein said seam is less than about 200 microns in width and about 200 microns in height.

6. The finger cover as in claim 1, wherein said seam is less than about 100 microns in width and about 100 microns in height.

7. The finger cover as in claim 1, wherein said seam is less than about 50 microns in width and 50 microns in height.

8. The finger cover as in claim 1, wherein at least one of said panels includes a texturized outer surface.

9. The finger cover as in claim 1, wherein an additional plurality of said reinforcement weld points are spaced around said seam.

* * * * *